(12) United States Patent
Dunne et al.

(10) Patent No.: US 9,119,924 B2
(45) Date of Patent: Sep. 1, 2015

(54) DISPENSING DEVICE, STORAGE DEVICE AND METHOD FOR DISPENSING A FORMULATION

(75) Inventors: Stephen T. Dunne, Stowmarket (GB); Thomas S. Reinhold, Muenster (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 966 days.

(21) Appl. No.: 13/148,813

(22) PCT Filed: Mar. 12, 2010

(86) PCT No.: PCT/EP2010/001574
§ 371 (c)(1),
(2), (4) Date: Oct. 19, 2011

(87) PCT Pub. No.: WO2010/105776
PCT Pub. Date: Sep. 23, 2010

(65) Prior Publication Data
US 2012/0037718 A1    Feb. 16, 2012

(30) Foreign Application Priority Data

Mar. 17, 2009 (EP) .................................. 09003802

(51) Int. Cl.
*A61M 16/00* (2006.01)
*B05D 7/14* (2006.01)
*A61M 15/00* (2006.01)

(52) U.S. Cl.
CPC .......... *A61M 15/0045* (2013.01); *A61M 15/005* (2014.02); *A61M 15/0026* (2014.02); *A61M 15/0043* (2014.02); *A61M 15/0048* (2014.02); *A61M 15/0051* (2014.02); *A61M 2202/064* (2013.01)

(58) Field of Classification Search
CPC ..................... A61M 15/0045; A61M 15/0026; A61M 15/0043; A61M 15/0048; A61M 15/005; A61M 15/0051; A61M 2202/064
USPC ......... 239/140, 141, 302, 310, 311, 316, 337, 239/338, 373; 128/203.15, 203.19, 203.21, 128/200.14; 604/58; 222/92, 95; 206/528, 206/530, 533, 535, 538, 539, 828
See application file for complete search history.

(56) References Cited

U.S. PATENT DOCUMENTS

| | | | |
|---|---|---|---|
| 4,627,432 A | 12/1986 | Newell et al. | |
| 5,415,162 A * | 5/1995 | Casper et al. | 128/203.12 |
| 5,533,502 A * | 7/1996 | Piper | 128/203.21 |
| 6,123,068 A | 9/2000 | Lloyd et al. | |
| 7,219,665 B1 * | 5/2007 | Braithwaite | 128/203.21 |

(Continued)

FOREIGN PATENT DOCUMENTS

| | | |
|---|---|---|
| EP | 1 087 750 B1 | 11/2003 |
| EP | 1 795 221 A1 | 6/2007 |

(Continued)

*Primary Examiner* — Justin Jonaitis
(74) *Attorney, Agent, or Firm* — Roberts Mlotkowski Safran & Cole, P.C.; David S. Safran

(57) ABSTRACT

A dispensing device, a storage device and a method for dispensing a formulation as a spray using a gas stream. Doses of the formulation are contained in storage members, which comprise individual atomizing device. The storage members are received in cavities, which are sealed by a common outlet seal. The outlet seal is peeled individually for each cavity to open the respective storage member and its atomizing device before the respective dose is dispensed by a gas stream flowing through the storage member.

11 Claims, 10 Drawing Sheets

(56) References Cited

U.S. PATENT DOCUMENTS

| | | | |
|---|---|---|---|
| 2003/0178024 A1* | 9/2003 | Allan et al. | 128/200.24 |
| 2007/0163574 A1* | 7/2007 | Rohrschneider et al. | 128/200.19 |
| 2007/0272763 A1 | 11/2007 | Dunne et al. | |
| 2008/0001008 A1* | 1/2008 | Thoemmes et al. | 239/338 |
| 2008/0283055 A1 | 11/2008 | Rohrschneider et al. | |
| 2009/0114220 A1 | 5/2009 | Wachtel et al. | |

FOREIGN PATENT DOCUMENTS

| | | |
|---|---|---|
| EP | 1 844 806 A1 | 10/2007 |
| EP | 2 077 132 A1 | 7/2009 |
| WO | 94/27653 A2 | 12/1994 |
| WO | 2005/002654 A2 | 1/2005 |
| WO | 2007/118343 A1 | 10/2007 |
| WO | 2008/138624 A1 | 11/2008 |
| WO | 2008/138631 A2 | 11/2008 |

* cited by examiner

DISPENSING DEVICE, STORAGE DEVICE AND METHOD FOR DISPENSING A FORMULATION

BACKGROUND OF THE INVENTION

1. Field of the Invention

The present invention relates to a dispensing device for dispensing a formulation as a spray. The preferably medical formulation particularly contains or consists of a drug or mixture of drugs, to a storage device for a dispensing device for dispensing a formulation as a spray, and to a method for dispensing individually doses of a formulation as a spray

2. Description of Related Art

Drugs delivered through dispensing devices, in particular inhalers, are intended to optimally target specific sites in the pulmonary system. These sites include the nasal passages, the throat, and various locations within the lungs, such as the bronchi, bronchioles and alveolar regions. The ability to deliver drugs to a target area depends inter alia on the aerodynamic sizes of the particles or droplets. As currently believed to be understood, particles having an aerodynamic diameter of less than 2 micrometer are considered to be potentially optimal for deposition in the alveolar region of the lung. Particles that have an aerodynamic diameter of between 2 and approximately 5 micrometer may be more suitable for delivery to the bronchiole or bronchi regions. Particles with an aerodynamic size range greater than 6 micrometer, and more preferably 10 micrometer, are typically suitable for delivery to the laryngeal region, throat or nasal passages.

In most cases, it is desired to achieve a high inhalable fraction and a high delivery efficiency, i.e., the fraction of the initial dose of drug that reaches the desired region, in particular in the lung. This depends on various factors, in particular on the characteristics of the generated spray plume, such as propagation velocity of the plume, particle size and its distribution, fraction of small particles, fraction of gas or the like. In the present invention, the desired spray plume characteristics include preferably a small particle size, a high fraction of drug particles with a diameter of 6 micrometer or less, a low propagation velocity and/or a long duration of spray generation and possible inhalation.

Most powder inhalers are of the passive type where the powder is inhaled by the patient without the aid of an additional energy source. The problem with passive inhalers is that the inhalable fraction, or the proportion of powder that actually enters the lungs, is largely dependent on the breathing of the patient. The transfer and de-agglomeration of the powder and hence the inhalable fraction is a function of the flow rate of inhaled air through the device and, therefore, varies greatly from patient to patient.

Dry powder inhalers are subdivided into single dose and multi-dose devices or inhalers. Multi-dose inhalers are further subdivided into pre-metered types where the doses are stored individually and into metering inhalers where each powder dose is metered in the device.

Multi dose pre-metered inhalers have the advantage that the single doses are metered under strict factory conditions and the powder can quite easily be isolated from the atmosphere. In many applications the active drug powder is mixed with a carrier such as lactose. The lactose and/or active drug(s) tend to absorb humidity from the atmosphere, which makes them stick together and difficult to transfer and de-agglomerate.

U.S. Pat. No. 4,627,432 discloses a device for administering medicaments to patients, namely an inhaler. The inhaler comprises a disk-like blister pack having a plurality of blister pockets arranged in a circle. Each blister pocket contains a dose of the powder. A plunger can open a blister pocket. When a blister is opened, the medicament can be withdrawn by a patient inhaling through a mouthpiece.

International Patent Application Publication WO 2005/002654 A2 discloses a passive device for dispensing individual doses of powder. The doses are contained in respective pockets of a disc-shaped carrier and opened by outwardly rupturing a foil lid in an axial direction by means of pressure on an opposite side surface. The pockets are moveable in axial direction into an airstream generated by breathing of a patient for dispensing a dose of powder from the pocket. The device provides individual respective deaggregation flow paths for each pocket, split airstreams allowing improved entrainment of powder, a cam mechanism for outwardly rupturing the pockets, an indexing mechanism linked to the cam mechanism, and a dose counter.

It is difficult to empty the respective pocket completely during a dispensing operation. Incomplete emptying results in decreased delivery efficiency. Some powder may be lost in the inhaler and not dispensed because the known solutions require relatively long paths for the powder until the powder reaches a nozzle and is actually dispensed. This might reduce the delivery efficiency further. In addition, de-agglomeration of the powder is difficult.

A good dispensing of pre-metered doses of the formulation can be achieved if individual atomizing devices, such as nozzles, are used to atomize the respective dose, i.e., to generate a spray or aerosol (the term "aerosol" can also be used if a powdered formulation is atomized). In the assignee's International Patent Application Publication WO 2008/138631 A2, the doses are contained in inserts as storage members, each comprising a respective atomizing device, in particular a duct, nozzle or the like. The inserts are moveably contained in cavities or receptacles and sealed. The inserts are moved outwardly to rupture the respective sealing before discharging the respective dose. This requires a respective actuation. The ruptured sealing may interfere with the generated spray. The outward movement requires respective space. Therefore, there is a need for a facilitated construction requiring less size and/or allowing a defined opening of outlet openings, in particular of atomizing devices. A similar dispensing device is disclosed in commonly owned U.S. Patent Application Publication 2008/0283055 A1

SUMMARY OF THE INVENTION

The present invention relates to the dispensing of a preferably medical formulation. The term "formulation" relates in particular to powder, but may include or relate to liquid as well. Consequently, the fine "particles" may be either solid or liquid. The term "liquid" has to be understood preferably in a broad sense covering inter alia solutions, suspensions, suslutions, mixtures thereof or the like. More particularly, the present invention relates to the dispensing of formulations for inhalation, such as medical formulations containing or consisting of at least one drug.

In the following, the description will focus mainly on powder formulations. However, the same applies for liquid formulations.

In particular, the present invention is concerned with dry powder inhalers for the delivery of drugs to the lungs. Many dry powder inhalers are on the market or have been proposed. There are two main types, namely the passive ones and the active ones. In passive inhalers all the energy required for de-agglomerating the powder and transferring the powder to the lungs is provided by the breathing of a user, respectively the patient. In active inhalers there is an additional source of energy to help to transfer and de-agglomerate the powder.

The present invention relates in particular to an active, gas (preferably air) powered, pre-metered multi-dose dispensing device for dispensing a formulation containing or consisting of a drug, such as a dry powder inhaler.

An object of the present invention is to provide an improved dispensing device, storage device and method for dispensing a preferably medical formulation, in particular allowing a facilitated construction requiring less size and/or allowing a defined opening of outlet openings, in particular of atomizing devices.

The above object is achieved by a dispensing device according to invention as described herein.

According to a first aspect of the present invention, the dispensing device comprises an opening device in addition to a connecting element for supplying pressurized gas individually to storage members containing the doses of the formulation. The opening device is adapted to individually open an outlet seal of an outlet opening for each storage member, wherein the opening device is adapted to work independently of any movement of the connecting element and/or to peel the seal. This allows a facilitated construction requiring less size and/or allowing or securing a defined and/or complete opening of outlet openings, in particular of atomizing devices.

According to a second aspect of the present invention, the storage device comprises inserts received in cavities or receptacles. Each insert comprises a storage chamber containing a dose of the formulation and an atomizing device, such as a duct or nozzle, for dispensing the respective dose as spray or aerosol. Outlet openings of the cavities, receptacles, inserts or atomizing devices are sealed by a preferably common outlet seal and can be opened individually. The inserts are unmovable in the cavities or receptacles. The outlet openings are opened independently of any movement of the inserts. This allows a facilitated construction requiring less size and/or allowing a defined opening of outlet openings, in particular of atomizing devices.

According to a third aspect of the present invention, the outlet openings of the storage device covered by a seal are individually opened by winding up the seal onto a wheel with spring-like arms and/or variable diameter. Thus, any potential variation of the winding speed can be compensated. This allows a facilitated construction requiring less size and/or allowing a defined opening of outlet openings, in particular of atomizing devices.

An advantage of the present invention is, in contrast to moveable inserts as storage members for foil opening, that peeling eliminates the possibility of a foil flap interfering with the insert exit ducts and thereby upsetting the flow pattern.

An advantage of the present invention is, in contrast to moveable inserts for foil opening, that peeling eliminates the possibility of any insert sealing foils being damaged when the insert is pushed out through the holder sealing foil. The insert foil could deform leading to an exit cross-sectional area that is less than that required. Peeling avoids this.

An advantage of the present invention is, in contrast to moveable inserts for foil opening, that the subassembly unit containing the spring and bellows requires less movement since the insert does not have to be pushed out.

An advantage of the present invention is, in contrast to moveable inserts for foil opening, that the failure possibility is less and that less push force is required.

An advantage of the present invention is, in contrast to moveable inserts for foil opening, that no feature is required to push inserts back during rotation and that the friction is less when rotating the carrier of the storage device with the inserts.

The above and other aspects and features of the present invention will be apparent from the following detailed description of preferred embodiments in conjunction with the accompanying drawings.

DETAILED DESCRIPTION OF THE INVENTION

In the figures, the same reference signs are used for the same or similar parts and components, wherein preferably the same or similar features, aspects and/or advantages are achieved in the different embodiments, even if a repetition of the respective description is omitted.

Figure 1:
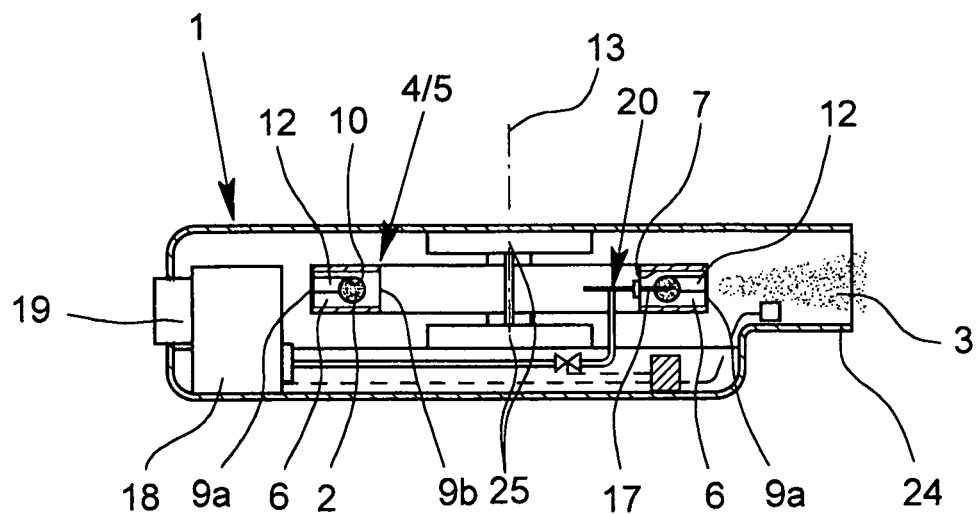
FIG. 1 is a schematic sectional view of a dispensing device with a storage device according to the present invention during dispensing.

FIG. 1 shows a schematic sectional view—for illustration purposes, not to scale—of a dispensing device 1 according to the present invention. The dispensing device 1 is preferably an active device, in particular gas powered. Preferably, the dispensing device 1 is an oral or nasal inhaler, in particular a dry powder inhaler, for a user.

Preferably, the dispensing device 1 is portable and/or handheld.

The dispensing device 1 may be used for dispensing any formulation 2 as defined in the introductory part of the description. In particular, a medical formulation 2 or a formulation 2 for inhalation will be used. The formulation 2 preferably contains or comprises at least one drug. When the formulation 2 is dispensed, a spray 3 is generated as indicated in FIG. 1. The spray 3 includes or is formed of fine particles (solid and/or liquid) and preferably has the desired spray plume characteristics.

The formulation 2 may be a liquid, in particular a solution, a suspension or any mixture thereof, i.e., a so-called suslution. Preferably, when different drugs are dispensed simultaneously, a suslution may be used. The principle of the suslution is based on that different drugs may be combined in one formulation simultaneously as a solution and as a suspension.

In this respect, reference is made to European Patent Application EP 1 087 750 A1, which is incorporated herein as additional disclosure in this respect.

Preferably, the formulation 2 is a powder. The powder may be a pure drug or a mixture of at least two drugs or any other mixture of at least one drug. In addition, the powder may contain at least one other material, in particular a drug carrier, such as lactose. In the following, the description focuses on powder as formulation 2. However, this applies in a similar manner if a liquid formulation 2 is used.

Preferably, the mean diameter of the powder particles is about 2 to 7 µm, in particular, 6 µm or less. This applies in particular if the powder does not contain any drug carrier, such as lactose.

If the powder contains a drug carrier, such as lactose, and at least one drug, the powder 2 may have a particle size of 20 to 300 µm, in particular about 30 to 60 µm. However, the de-agglomeration, which will be described later in more detail, may result even in this case in a spray 3 with a smaller particle size, e.g., of about 10 µm or less. In particular, the drug may be separated from the drug carrier during de-agglomeration so that primarily the drug will be inhaled due to its small particle size of about 2 to 6 µm and the larger drug carrier will be swallowed when using the dispensing device as an inhaler. Alternatively or additionally, breaking or opening of the drug carrier is possible during de-agglomeration.

The diameters mentioned above and below may be understood as mass medium aerodynamic diameters and/or may apply to the particle size or a fraction of the particles of the spray 3.

Preferably, the formulation 2 is pre-metered in separate or individual doses, which can be discharged one after the other by the dispensing device 1, in particular, for inhalation.

The dispensing device 1 is adapted to receive or comprises a storage device 4 for storing preferably multiple and pre-metered doses of the formulation 2. The storage device 4 may be integrated into the dispensing device 1 or form part of the dispensing device 1. Alternatively, the storage device 4 may be a separate part that can be inserted or connected with the dispensing device 1 and optionally replaced.

Figure 2:
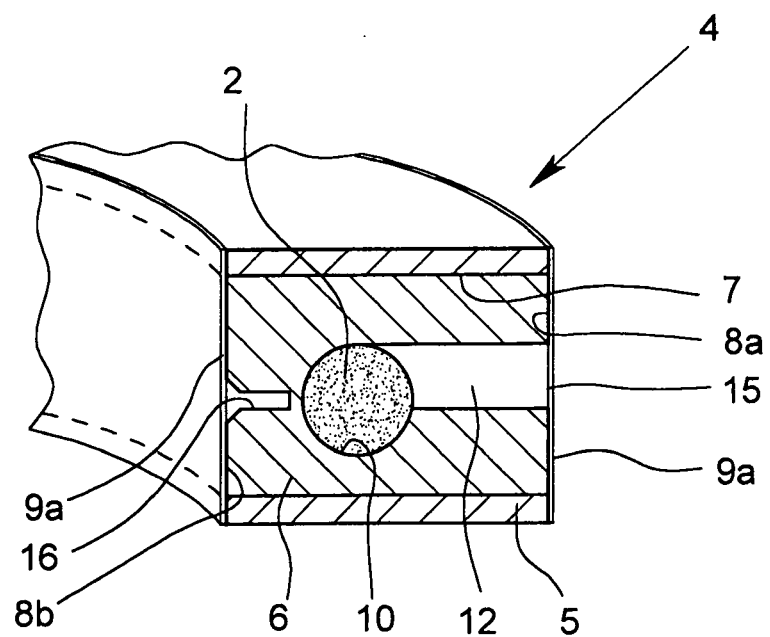
FIG. 2 is a schematic sectional perspective view of the storage device with an insert.
Figure 3:
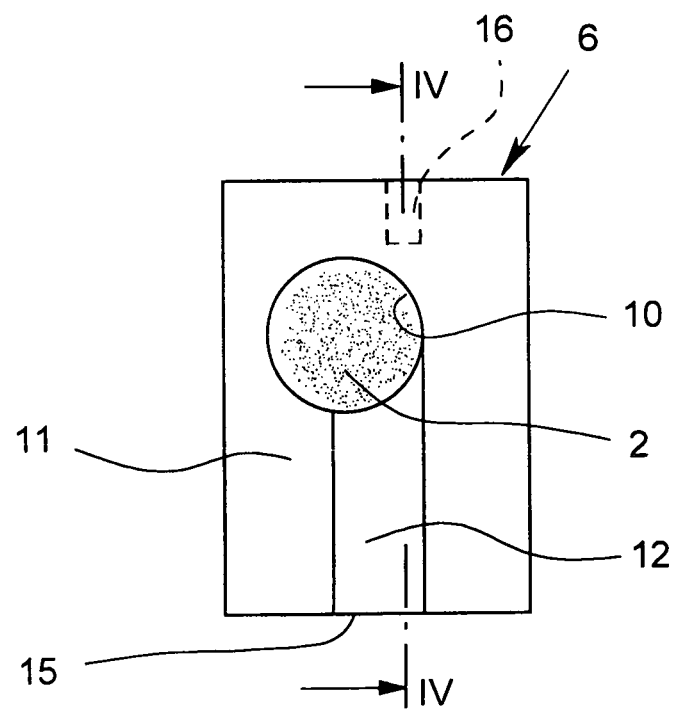
FIG. 3 is a schematic sectional view of the insert.

FIGS. 2 & 3 show a schematic cross sections of a part of the preferably ring-shaped storage device 4. The storage device shown here is like that shown in FIGS. 2 & 3 of commonly owned, co-pending U.S. patent application Ser. No. 12/120,803, which is the above noted U.S. Patent Application Publication 2008/0283055 A1, and is hereby incorporated by reference.

The storage device 4 preferably comprises a carrier 5 and at least one storage member, preferably multiple storage members. Preferably, the storage members are inserts 6. Therefore, the word "insert" is used in the following.

In particular, the carrier 5 may comprise or support 20 to 100, preferably 30 to 60 inserts 6. Each insert 6 contains preferably one pre-metered dose of the formulation 2. However, each insert 6 may also contain more than one formulation 2, i.e., different formulations 2. Additionally or alternatively, different inserts 6 may contain different formulations. In the present invention, "different" means, in particular, that the formulations 2 differ in at least one of the composition, the drug, the dose or amount, the concentration, and consistence of the formulation 2, e.g., liquid or dry powder.

The storage device 4 or carrier 5 comprises preferably multiple cavities 7 or receptacles for receiving or with the inserts 6. In particular, each insert 6 is located in a separate cavity 7. Preferably, the cavities 7 are separate from each other and, in particular, sealed against each other.

In the present embodiment, each cavity 7 comprises at least one outlet opening 8a, in particular, also an opposed receiving opening 8b (here, at the radially inner and outer circumference or periphery).

The cavities 7 or its openings 8 are covered by respective covers or seal 9a, 9b, which are, preferably, formed by heat-sealed foils on opposite sides of the respective cavity 7 or the carrier 5. In the present embodiment, the seals are in particular a metallic foil, such as aluminum foil, a plastic foil, a multi-layer arrangement or the like. The seals preferably protect the inserts 6 and/or formulation 2 against humidity, dirt, moisture and/or the like. The seals are respectively resistant and/or impermeable, in particular gas-tight.

In this preferred embodiment, the storage device 4 or carrier 5 is ring-like and the cavities 7 and/or inserts 6 extend at least substantially in radial direction. The cavities 7 are distributed around the perimeter of or along the storage device 4 or carrier 5, preferably equally spaced relative to the adjacent cavities 7.

The outlet openings 8a and/or outlet ends of the insert 6 are covered by a preferably common seal 9a, which extends ring-like or along the circumference. The receiving openings 8b are covered by the preferably common inner sailing 9b, which extends preferably ring-like or along the circumference.

In the present embodiment, the storage device 4/carrier 5 is preferably rotatable around axis 13 shown in FIG. 1. In particular, the dispensing device 1 can be opened and the storage device 4/carrier 5 can be inserted or replaced.

The carrier 5 may be a molded element, a ring, a strip, a cartridge, a blister or a container. Preferably, the storage device 4 or carrier 5 is rigid or at least essentially stiff.

Preferably, the carrier 5 is made of foil, plastics, ceramics and/or composite material, in particular of thermoplastics or thermoplastic elastomers.

Each cavity 7 or receptacle preferably forms a holder for the associated insert 6, in particular so that the insert 6 is not moveable in a direction toward the outlet, i.e., outwards of its outlet opening 8.

FIG. 1 shows a situation, where the insert 6 or cavity 7 or outlet opening 8a on the right side has already been opened, i.e., the outlet seal 9a has been opened or removed, preferably peeled. The insert 6 shown on the left side of FIG. 1 is still within its closed and sealed cavity 7.

Each insert 6 is preferably produced filled with the respective dose of formulation 2 separately from the storage device 4 or carrier 5, and then, inserted into its respective cavity 7 or receptacle.

Preferably, each insert 6 is molded and/or made of foil, plastics, ceramics and/or composite material, in particular of thermoplastics or thermoplastic elastomers and for seals of elastomers or silicone.

According to a preferred embodiment, the carrier 5 and/or the inserts 6 are made of at least one of the following materials or any mixture or blend thereof: ABS (acrylonitril-butadiene-styrene copolymer); SAN (styrene-acrylonitril-copolymer); PBT (polybutylene terephthalate); PC (polycarbonate); CA (cellulosic acetate); EVA (ethylene vinylacetate copolymer); PA (polyamide); PE (polyethylene); PP (polypropylene); PMMA (polymethylmethacrylate); POM (polyoxymethylene, polyacetal); PPS (polyphenylene sulfide); PS (polystyrene); PBTP (polybutylene terephthalate); TPU (thermoplastic polyurethane); blend of PC and PBTP; blend of PC and ABS; LCP (liquid crystal polymers); PHCS (polypyrrol or polythiophene); PPA (polyphthalamide); PSU (polysulfone); PTFE (polytetrafluorethylene); PUR (polyurethane); SB (styrene-butadiene copolymer); PIB (polyisobutylene); PAN (peroxyacylnitrate); PET (polyethylene terephthalate); AMMA (acrylonitril-methymethacrylat copolymer); PAR (polyarylate); PEEK (polyetheretherketone); COC (cycloolefine copolymer).

Each insert 6 may form a preferably block-shaped unit and/or be rigid. Alternatively, the inserts 6 may be flexible. In particular, each insert 6 may be a unitary unit or is formed of multiple elements. In particular, the insert 6 forms one component or is made of one piece. Each insert 6 may be a molded element, a cartridge, a blister, a capsule, a container or the like.

In the following, a preferred construction of one insert 6 is explained. Preferably, all inserts 6 are identical. However, it is also possible that all or some inserts 6 are different. For example, two or more groups of different inserts 6 can be provided. It is possible that one group has a different dose or different formulation 2 than the other group. For example, the inserts 6 of the different groups could be arranged alternately one after the other so that a patient or user may use, for example, an insert 6 of one group each morning and an insert 6 of the other group each evening.

Figure 4:
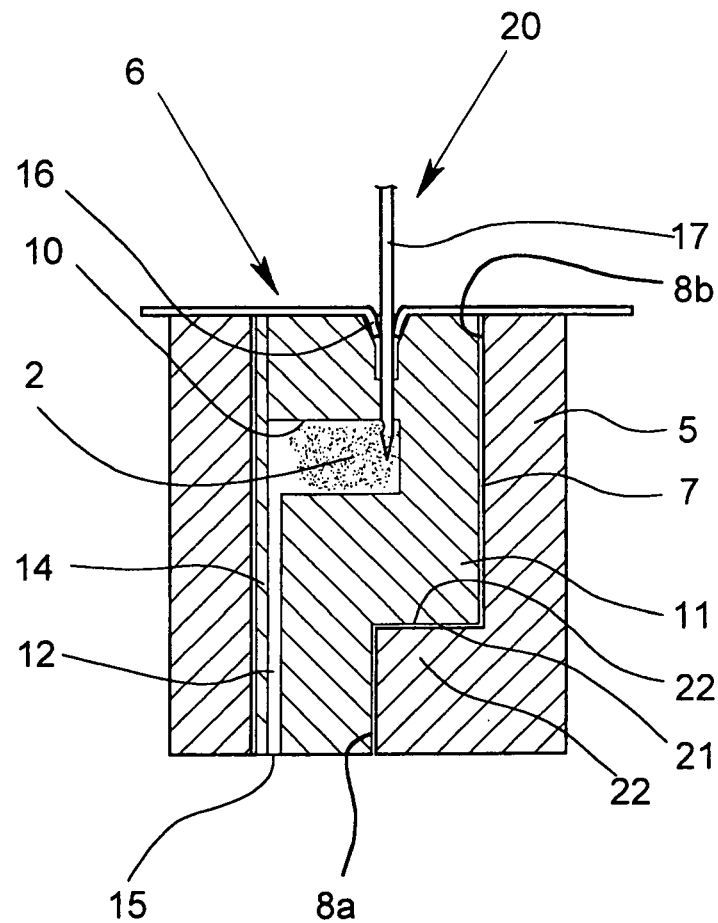
FIG. 4 is a schematic sectional view of the insert mounted in a cavity taken along line IV-IV in FIG. 3.

Each insert 6 preferably comprises a storage chamber 10 for a single dose of the formulation 2. The schematic sectional views according to FIGS. 2 and 3 show a preferred embodiment of the insert 6. The schematic sectional view according to FIG. 4, being taken along line IV-IV of FIG. 3, shows the insert 6 in the carrier 5 when the insert 6 or respective cavity or outlet opening 8a has been opened.

In the present embodiment, the storage chamber 10 is preferably formed in a molded base member 11 of the insert 6.

The insert 6/base member 11 further comprises an individual atomizing device, such as a duct 12, nozzle or the like, for de-agglomerating and/or discharging the formulation 2 during the dispensing operation, in particular, for atomizing the formulation 2. The formulation 2 is dispensed through the atomizing device during the dispensing operation, in particular for directly forming the spray 3.

In the present embodiment, the duct 12 is flat and/or rectangular in cross section. In particular, the cross section corresponds to a hydraulic diameter of less than 1 mm. In particular, the duct 12 is designed as described in International Patent Application Publication WO 2006/037636 A2 and corresponding, commonly owned, co-pending U.S. patent application Ser. No. 12/120,803 (Publication 2007/0272763 A1), which are hereby incorporated by reference.

According to another embodiment (not shown), the duct 12 can also be used as a reservoir (storage chamber 10) for the formulation 2. In this case, the separate storage chamber 10 is not required. Then, the duct 12 is designed to enable sufficient mixing of the gas with the formulation 2 and sufficient de-agglomeration of the powder formulation 2.

Preferably, the spray 3 having its desired spray characteristics is directly ejected or discharged from the insert 6/atomizing device or is generated by the atomizing device only.

In particular, the insert 6 forms one component or is made of one piece.

The insert 6 or atomizing device can comprise or form a nozzle arrangement, preferably at an outlet 15 or end of duct 12 or formed by duct 12.

Preferably, the storage chamber 10 and/or the atomizing device or duct 12 is formed by or in the base member 11, in particular by a recess, groove or the like in the base member 11 and by an associated cover member 14 as shown in FIG. 4. In particular, the duct 12 forms a channel from the storage chamber 10 to an outlet opening 15 of the insert 6 or atomizing device in particular for directly discharging or dispensing the formulation 2 as spray 3 as shown in FIG. 1. Preferably, the base member 11 is molded and/or rigid. Preferably, the cover member 14 is rigid and/or rigidly fastened, e.g., welded, to the base member 11.

It is noted that the inserts 6 may be or are preferably open, i.e., not sealed, in particular, at its respective outlet opening 15 only. Experiments have shown that sealing of the carrier 5/the cavity 7 is sufficient. The duct 12 or outlet opening 15 is preferably so small in cross section or provided with a bursting element or any other suitable means that the formulation 2 is not discharged, preferably even with opened seals and/or during strong shaking of the dispensing device 1/storage device 4, but preferably only when gas (air) is forced through the insert 6 and atomizing device or duct 12.

The inserts 6 and cavities 7 are preferably adapted to each other such that at least the outlet seal 9*a* or both seals contact end faces of the inserts 6 and, thus, cover the outlet openings 15. This may (further) prevent that any formulation 2 dissipates through the duct 12/outlet opening 15 before the desired dispensing. In order to increase the sealing or cover effect by seal 9*a*, the inserts 6 may be slightly longer than the cavities 7 and/or protrude at its outlet side and/or be pressed with its outlet openings 15 against the respective seal 9*a* or vice versa.

The insert 6 comprises preferably an inlet for supplying preferably pressurized gas into the storage chamber 10 to force the formulation 2 through the atomizing device and to directly generate the described spray 3. In the present embodiment, the inlet is preferably formed by a weak or thinned portion and/or designed as a preferably tube-like recess 16 or blind bore preferably formed in the base member 11. Preferably, the recess 16 is not directly connected to the storage chamber 10, but separated by a seal or an intermediate or thinned wall or the like. This wall can be penetrated e.g., by a connecting element, preferably a piercing element 17 such as a needle as shown schematically in FIGS. 1, 4 and 5 or by any other suitable opening, connecting and/or supply means, in particular when the respective insert 6 is connected to a gas supply as explained in the following. Preferably, the piercing element 17 is a hollow needle for supplying the pressurized air into the insert 6/storage chamber 10.

In the present invention, the expression "piercing element 17" preferably covers also all other suitable types of means for opening and/or connecting the storage device 4, the carrier 5, a cavity 7 and/or an insert 6 and/or for directly or indirectly supplying gas to an insert 6 or its respective storage chamber 10.

The duct 12 is preferably at least tangentially connected to the storage chamber 10 as shown in FIGS. 2 & 3. Preferably, the duct 12 is connected at one axial end of the preferably cylindrical chamber 10, and the gas inlet (recess 16/piercing element 17) is connected or connectable to the other axial end of the chamber 10 as indicated in FIG. 4. In particular, the gas inlet is connected also tangentially to the storage chamber 10, such that swirls are generated when entering the gas with a swirl direction supporting discharge of the mixture of gas and formulation 2 through the duct 12, which connects tangentially to the rotational direction of the swirl.

The dispensing device 1 uses preferably pressurized gas, in particular air, to force the formulation 2 through the atomizing device or duct 12 to de-agglomerate the powder and/or to generate the spray 3 with fine powder particles. Preferably, the dispensing device 1 comprises a means for providing pressurized gas, in the present embodiment an air pump 18, as indicated in FIG. 1, which can preferably be actuated or operated manually, e.g., as indicated by handle or actuator 19 and/or by a spring means as shown later in another embodiment.

In particular, the air pump 18 comprises or is formed by a bellows 27 as schematically shown e.g., in FIG. 5. But, it could be also a piston-cylinder-arrangement. Instead of the air pump 18, the means for providing pressurized gas can be e.g., a capsule, container or the like containing pressurized or liquefied gas for powering the dispensing device 1, i.e., dispensing the formulation 2 as desired. Therefore, the term "means for pressurizing gas" is to be understood in a broad sense to cover these and similar alternatives to the pump 18 as well.

The means for providing pressurized gas/air pump 18 may provide a gas pressure of less than 300 kPa, in particular about 50 to 200 kPa. This is preferably sufficient for operating the dispensing device 1. If liquefied gas or a container with pressurized gas is used, the gas pressures might range from 100 kPa to about 700 kPa. Then, the pressure may be reduced or throttled to the preferred pressure range before supplying the gas to the storage device 4, in particular the storage chamber 10, of the respective insert 6.

Preferably, all pressure values mentioned in the present description are gauge pressures, i.e., pressure differences. All pressure values relate to the pressure in a gas storage, such as a container with pressurized or liquefied gas or provided by air pump 18 or relate to the pressures acting in the chamber 10 and/or in the duct 12.

Figure 5:
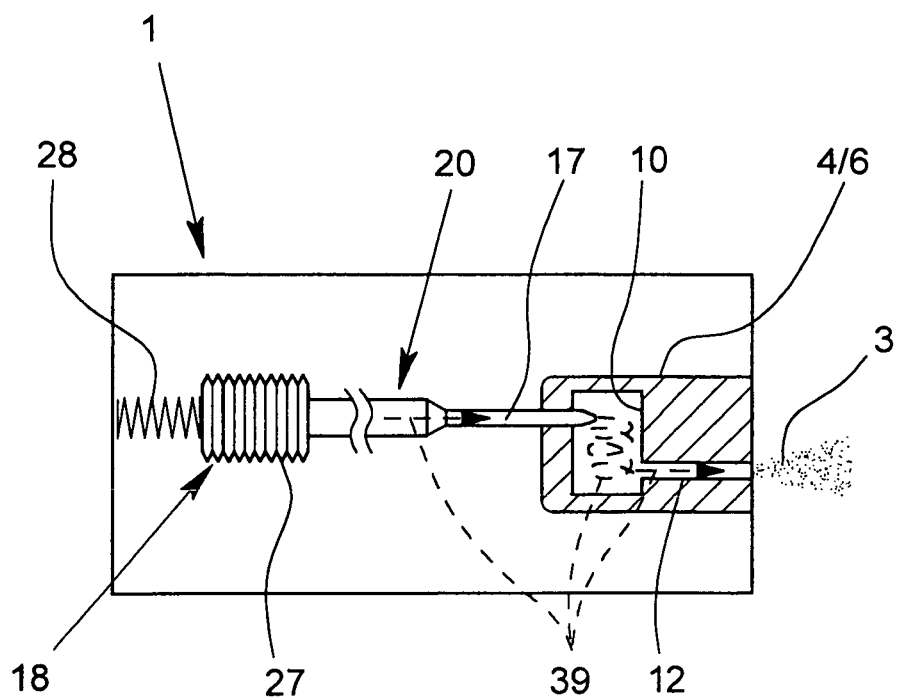
FIG. 5 is schematic sectional view of the storage device with a pierced insert.

FIGS. 1 & 5 show that the dispensing device 1 preferably comprises a mechanism 20 for individually connecting the gas supply or connecting element to the inserts 6, preferably by a connecting movement of the connecting element.

In particular, in an operation phase, the piercing element 17 penetrates the inner sealing 9b and is inserted into the recess 16 and through the intermediate, end or weakened wall into the storage chamber 10, and thus, connects the respective insert 6 to the gas supply.

The insert 6 may be held by force-fit or by form-fit in the associated cavities 7 or receptacles or in the carrier 5. In the present embodiment, the cavity 7 or carrier 5 comprises a stop 21 against which a front face or shoulder 22 abuts, in particular so that the insert 6 is securely held within the cavity 7 even if the insert 6 is pierced by the piercing element 17.

Before, simultaneously or afterwards, an opening operation takes place. The insert 6, cavity 7 or receptacle and/or outlet seal 9a is opened at the outlet side. The final situation is shown in FIG. 1 on the right side and in FIGS. 4 & 5.

Figure 6A:
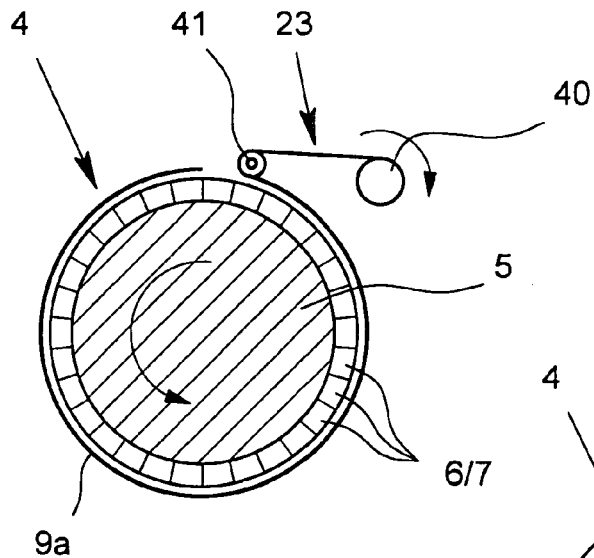
FIG. 6a is a schematic view of a first peeling concept for opening the storage device.

The dispensing device 1 preferably comprises an opening device 23 which will be explained with reference to the very schematic view shown in FIG. 6a. Preferably, the opening device 23 is provided in addition to the connecting element. The opening device 23 is provided for opening the outlet seal 9a or outlet openings 8a, 15 individually. The opening device 23 is adapted to work independent of the connecting movement.

Preferably, the outlet seal 9a is peeled. Therefore, the opening device 23 is preferably adapted to peel the outlet seal 9a.

In the illustrated embodiment, the peeled outlet seal 9a is wound up. The opening device 23 comprises preferably a wheel 40 for winding up the outlet seal 9a.

The wheel 40 is preferably driven and in particular coupled with the indexing movement or rotation of the storage device 4 or carrier 5. In particular, the wheel 40 is drivingly and/or possibly coupled with the storage device 4, carrier 5 or its drive. In the embodiment according to FIG. 6a, the wheel 40 is rotated in the direction opposite from the storage device 4/carrier 5.

It is also possible that the peeling or tension of the outlet seal 9a drives the storage device 4 or carrier 5, i.e., the opening device 23 may form the drive for indexing or rotating the storage device 4, carrier 5 or ring of inserts 6/cavities 7. In particular, the wheel may be driven to rotate.

The opening device 23 comprises preferably at least one guide element 41 which is preferably located adjacent to the outer periphery of the storage device 4 or carrier 5 or annular arrangement of the cavities 7 or receptacles or adjacent to the outlet openings 8a, 15. The guide element 41 allows determined peeling with in particular constant peeling or shearing angle. The guide element 41 may be a loose or driven roll or wheel or an unmovable or an unrotatable member.

The guide element 41 may be moveable in a radial direction or biased against the fixed seal 9a or towards the cavities 7 or openings 8a, 15, e.g., by the tension and guidance of the peeled seal 9a and/or by a spring means or the like.

Consequently, the insert 6 is no longer required to move out of its cavity 7 or receptacle to rupture the outlet seal 9a. Instead, the outlet seal 9a is peeled off the insert ring or opened or removed in any other manner.

It is noted that the guide element 41 is only optional. It is also possible that the wheel 40 directly winds up the outlet seal 9a.

The winding up speed of the wheel 40 and the speed of rotation of the storage device 4, carrier 5 or ring of cavities 7 or inserts 6 are preferably identical such that the newly opened cavity 7 is always at the same rotational position of the ring arrangement so that the outlet direction during dispensing remains the same.

Figure 6B:
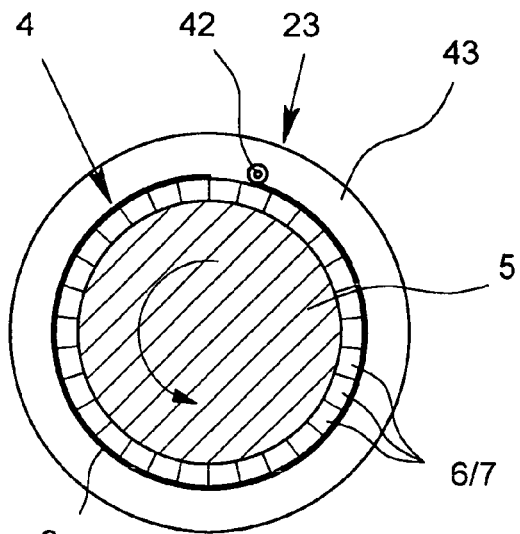
FIG. 6b is a schematic view of a second peeling concept for opening the storage device in a first state.
Figure 6C:
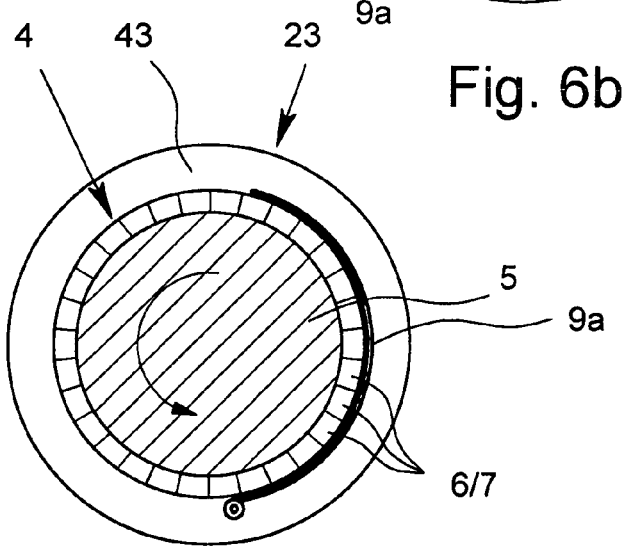
FIG. 6c is a schematic view of the second peeling concept for opening the storage device in a second state.

FIGS. 6b & 6c explain another embodiment of the opening mechanism or opening device 23. Here, the peeled outlet seal 9a is preferably not wound-up, but drawn away or preferably around the outer periphery of the storage device 4, carrier 5 or ring of receptacles containing the inserts 6.

In this embodiment, the opening device 23 comprises a holding element 42 which is connected with an end of the outlet seal 9a and which is moveable relative to the storage device 4 or carrier 5, in particular along their outer periphery or on a circular path relative to the storage device 4, carrier 5, ring of inserts 6/cavities 7 or fixed outlet seal 9a. Thus, the outlet seal 9a may be peeled by drawing the peeled part away or preferably over the still fixed part of the outlet seal 9a.

FIG. 6b shows more or less the beginning of the peeling where most inserts 6 or cavities 7 are still covered by the outlet seal 9a. FIG. 6c shows a later stage where more or less half of the inserts 6/cavities 7 have been opened, i.e., where more or less half of the outlet seal 9a has already been peeled. FIG. 6c shows that the holding element 42 is preferably moveable on a circular path in opposite direction of the insert 6/cavity 7 or the storage device 4 or carrier 5 during the indexing or rotation.

Preferably, the holding element 42 is moveable by a counter rotating part 43 such as a ring or other like, and/or is drivingly connected with the carrier 5, e.g., by means of meshing gears (not shown), in particular such that the part 43 counter-rotates relative to carrier 5.

It is noted that the opening device 23 is responsible for the opening operation. In particular, the cavities 7, inserts 6, atomizing devices or its outlet opening 8a, 15 are individually opened, i.e., for each storage member/insert 6 separately or stepwise. Instead of peeling, the outlet seal 9a can be steered, pierced, removed or opened in any other suitable form than already described. For example, the outlet seal 9a could be removed or peeled only partially, e.g., only a lengthwise part or strip of the seal 9a.

After the connecting operation and opening operation, the dispensing device 1 is activated and ready for dispensing the respective dose of the just opened storage member/insert 6.

For dispensing, the pressurized gas (air) is supplied to the storage chamber 10 via the piercing element 17 or any other suitable connecting or supply element. The gas (air) generates a respective flow in the storage chamber 10 to mix gas and powder and to force the dose through the atomizing device or duct 12.

FIG. 5 shows a preferred construction or design of the dispensing device 1. In this embodiment, the means for pressurizing gas (air pump 18) comprises the bellows 27 for pressurizing gas, in particular air. The bellows 27 may be actuated by a spring means, in particular, a spring 28 as schematically shown. In particular, the spring means compresses the bellows 27 during the dispensing operation to pressurize the gas and to supply the gas to the connected storage device 4/storage member/insert 6/storage chamber 10 via the connecting or supply mechanism 20/connecting element/piercing element 17. Thus, a gas stream is generated as shown by arrows 39 during the dispensing operation. The gas stream 40 flows through the storage device 4/storage chamber 10, entrains the respective dose of the formulation 2 and is ejected via the atomizing device or duct 12 to generate the spray 3 as schematically shown in FIG. 5. However, other constructions, in particular of the means for pressurizing gas, are possible.

Preferably, the dispensing device 1 or storage device 4 or means for pressurizing gas comprises a throttle for throttling the gas stream 39. In the present embodiment, the throttle is formed by a restriction and/or the connecting element, i.e., here by the hollow needle or piercing element 17. However, other constructional solutions are possible.

Preferably, the throttle is located stream up, in particular just before, the storage chamber 10. However, it is also possible to form the throttle within the storage chamber 10 or downstream thereof, in particular in or by the duct 12 or the like.

The powder will be discharged—in particular forced through the atomizing device or duct 12—with a comparatively low gas pressure (preferably less than 300 kPa, in particular about 50 to 200 kPa). This low gas pressure, which is significantly lower than the gas pressures in the prior dispensing devices, enables a respectively low discharge velocity and, therefore, a slow spray 3 with slow propagation velocity.

Preferably, the storage chamber 10 forms a mixing chamber for mixing the gas with the powder. The chamber 10 is preferably designed such that the gas can generate swirls or eddies for better mixing the powder with the gas. Preferably, the chamber 10 is substantially circular in cross section, in particular cylindrical. However, other shapes are also possible.

Further, the chamber 10 is formed with no sharp edges, corners or the like, but has a smooth contour so that the gas can sweep all chamber surfaces to prevent powder accumulating on said surfaces and to ensure or allow complete discharge of the powder. In particular, the gas inlet formed by the piercing element 17 or any other supply element is located opposite to the outlet, i.e., duct 12 and/or nozzle, with regard to the axial or outlet direction.

During the dispensing operation, the spray 3 is preferably directly or only generated by the respective insert 6 or its atomizing device or duct 12 and outputted into a mouthpiece 24 of the dispensing device 1 as shown in FIG. 1 for inhalation by a patient or user (not shown).

After dispensing one dose or before or for dispensing the next dose, the piercing element 17 will be withdrawn from the connected insert 6.

Then, the carrier 5 will be indexed one step further or to the next insert 6, in particular rotated by means of an indexing or transport mechanism (not shown). This mechanism is preferably operated by actuating the actuator 19 or any other means, by opening a cap or cover of the dispensing device 1 or the like, as already mentioned.

It is noted that the present invention, in particular the dispensing device 1 and/or the storage device 4, can be used for dispensing one drug, a blend of drugs or at least two or three separate drugs. In the latter case, the separate drugs are stored in separate storage chambers 10, and during the dispensing operation, the drugs are mixed either in a common mixing chamber or in their respective storage chambers 10 with the gas. Further, the separate drugs can be discharged through a common duct 12 or through separate ducts 12. In the latter case, the separate drugs will be mixed after leaving the separate ducts 12 or in the mouthpiece 24 or in any other suitable (additional) mixing chamber. It is also possible to mix the separate drugs by impinging jets of the separate drugs. For dispensing the separate drugs, it is preferred to use a common gas supply or means for pressurizing gas such as air pump 18.

Preferably, the spray 3 has a mean velocity (taken 20 cm from the outlet 15 or mouthpiece 24) of less than 2 m/s, in particular less than 1 m/s. Preferably, the mean duration of the spray 3 is at least 0.2 or 0.3 s, in particular about 0.5 to 2 s.

In the preferred embodiment according to FIG. 1, the cavities 7 are orientated in tangential or radial direction of the storage device 4 or carrier 5. Consequently, the connecting movement runs preferably in tangential or radial direction, in particular outwardly, in order to connect the respective insert 6 for dispensing the respective dose of the formulation 2 as indicated in FIG. 1. Accordingly, the mechanism 20 preferably operates in a radial direction for connecting the inserts 6 individually to the gas supply. This radial movement allows a very compact design of the dispensing device 1, in particular in axial direction.

Preferably, the mouthpiece 24 and the dispensing direction extend in radial or tangential direction as shown in FIG. 1.

Preferably, the dispensing device 1 comprises a lever or handle (not shown) or the actuator 19 or any other driving or actuation means for preferably manual actuation in order to index the carrier 5 one step further, i.e., to the next insert 6, and/or to operate the mechanism 20, preferably to connect the respective insert 6 to the gas supply and/or to operate opening device 40.

It is noted that the dispensing device 1 preferably operates only mechanically.

According to another embodiment (not shown), the inserts 6 may be formed as capsules, blister pockets or the like without any duct 12, or the like. Instead, each insert 6 is connected individually to a gas supply and to a common outlet arrangement, such as a duct 12, nozzle or the like for dispensing the respective dose of the formulation 2.

According to another embodiment, a secondary packaging may be used for packing and protecting the storage device 4/carrier 5, in particular for storage purposes before inserting the storage device 4/carrier 5 into the dispensing device 1. Additionally the whole device 1 including the storage device 4/carrier 5 may be stored in a secondary water vapor proof packaging.

According to another embodiment, the dispensing device 1 may also be a passive inhaler wherein a patient or user (not shown) forces sucks an air flow through the respectively opened insert 6, when breathing in so that this airflow entrains the formulation 2 and forms the desired spray 3 in the mouthpiece 24 for inhalation by the patient/user.

According to a further embodiment, the dispensing devise 1 may be breath activated, in particular wherein the formulation 2 is only released after the patient's or user's inhalation rate has reached a predetermined level, preferably by the use of a pressure sensitive means, such as a bursting element, membrane or valve, or any other mechanism.

It is noted that the term "dispensing device" has to be understood preferably in a broad sense to include other discharge devices, dispensers or the like, preferably wherein the formulation 2 or any other fluid is sprayed or atomized only when needed, in particularly discontinuously.

In the following, a further preferred embodiment of the dispensing device 1 will be explained with reference to FIGS. 7-10 of the drawings which correspond to FIGS. 7-10 of the above mentioned commonly owned, co-pending U.S. patent application Ser. No. 12/120,803 (Publication 2007/0272763 A1). The following description will focus on relevant differences between the further embodiment and the previous embodiments as well as the features of FIG. 11 rhat have no counterpart in application Ser. No. 12/120,803. In particular, the previous explanations and descriptions apply accordingly and/or additionally, even if not repeated.

Figure 7:
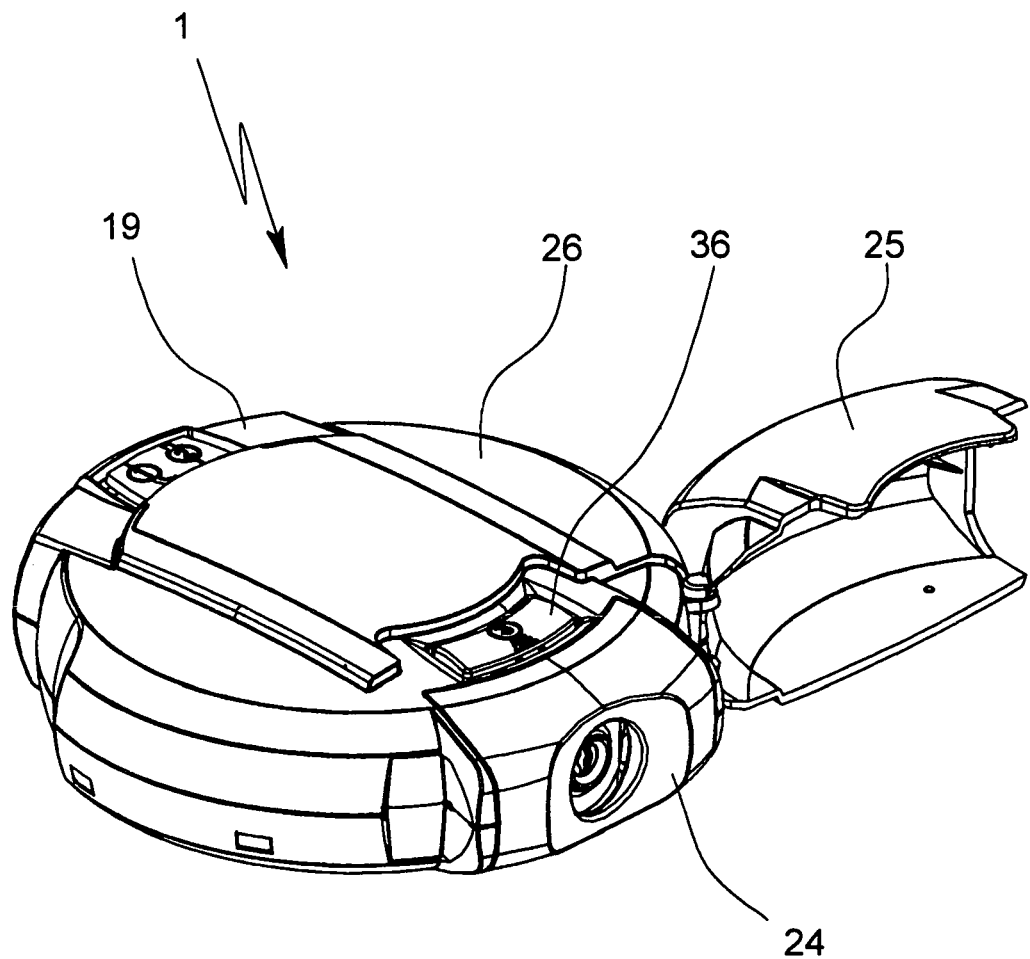
FIG. 7 is a schematic perspective view of a dispensing device according to a further embodiment.

FIG. 7 shows the further embodiment of the dispensing device 1 in a perspective view. The dispensing device 1 comprises a cover 25 for covering the mouthpiece 24. Preferably, the cover 25 can be pivoted to open or uncover the mouthpiece 24 as shown. Preferably, the mouthpiece 24 is snapped to a housing 26 of the dispensing device 1.

The dispensing device 1 comprises the actuator 19 at one side of housing 26, preferably on the opposite side from the mouthpiece 24 and/or opposite the main spray direction (preferably in a radial direction) of the dispensing device 1. The actuator 19 preferably forms a grip or handle. Therefore, the term "grip" will be used in the following.

The grip 19 is preferably moveable in a radial direction for actuating the dispensing device 1 as explained later in more detail. In particular, the grip 19 can be pulled radially outwardly from the initial position shown in FIG. 7 and pushed back into its initial position. These operations may be named "pulling" and "pushing", respectively, in the following. However, it is noted that these operational movements could also be realized by any other direction or type of movement, such as a non-translational movement.

Figure 8:
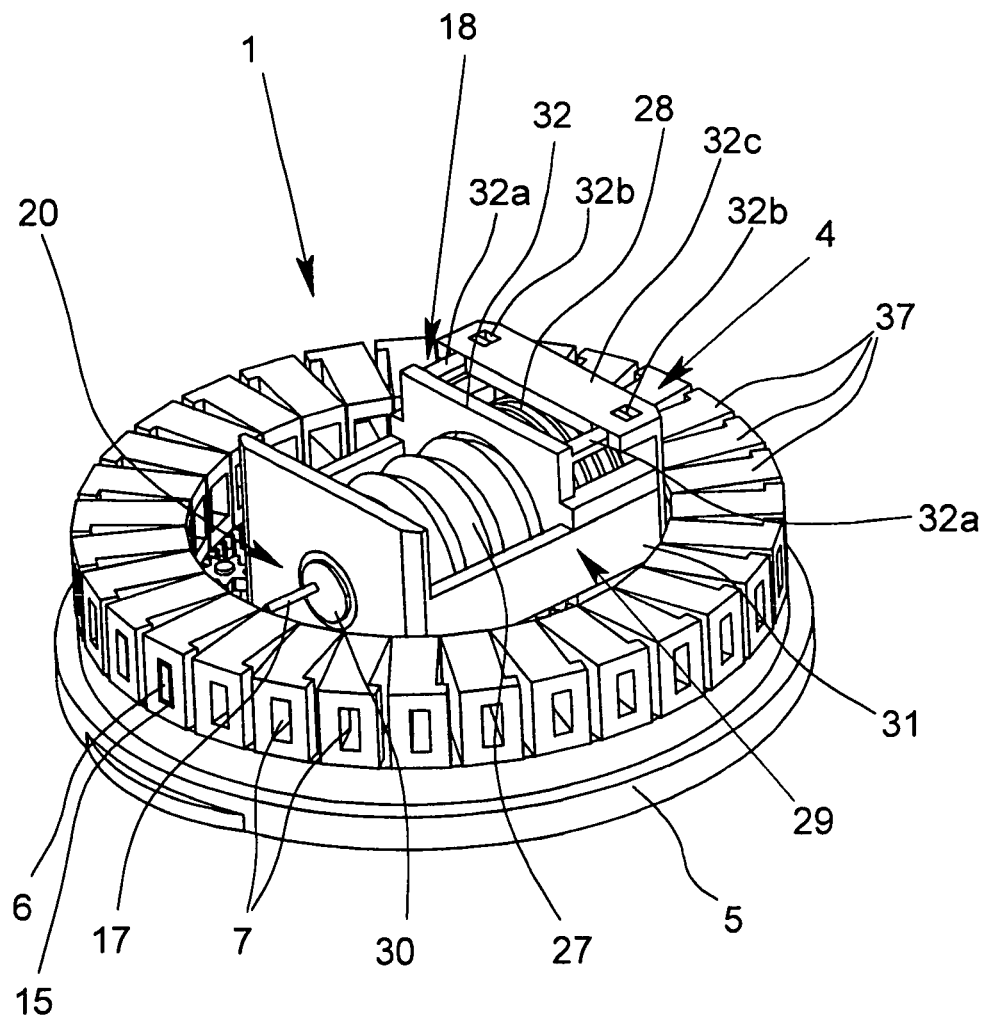
FIG. 8 is a schematic perspective view of inner components of the dispensing device according to FIG. 7 with retracted air assembly.
Figure 9:
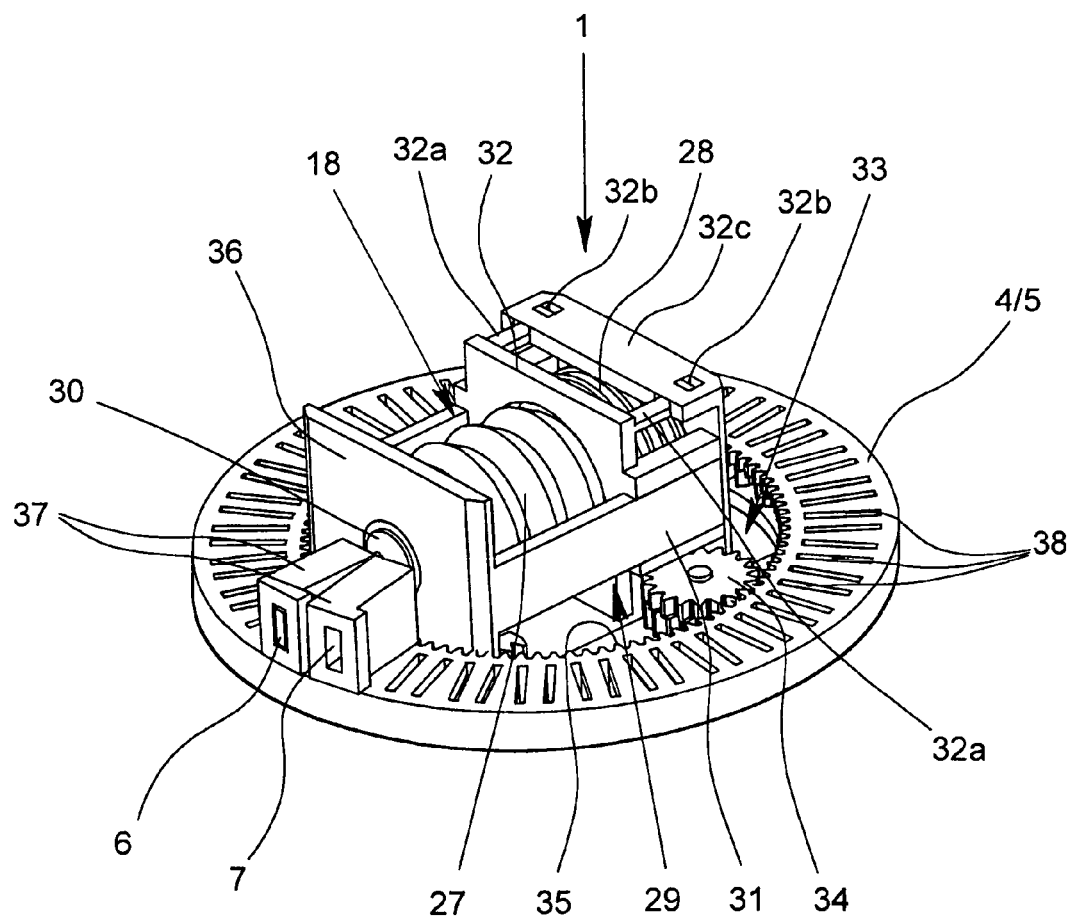
FIG. 9 is a schematic perspective view of inner components of the dispensing device according to FIG. 7 with advanced air assembly in an activated state.
Figure 10:
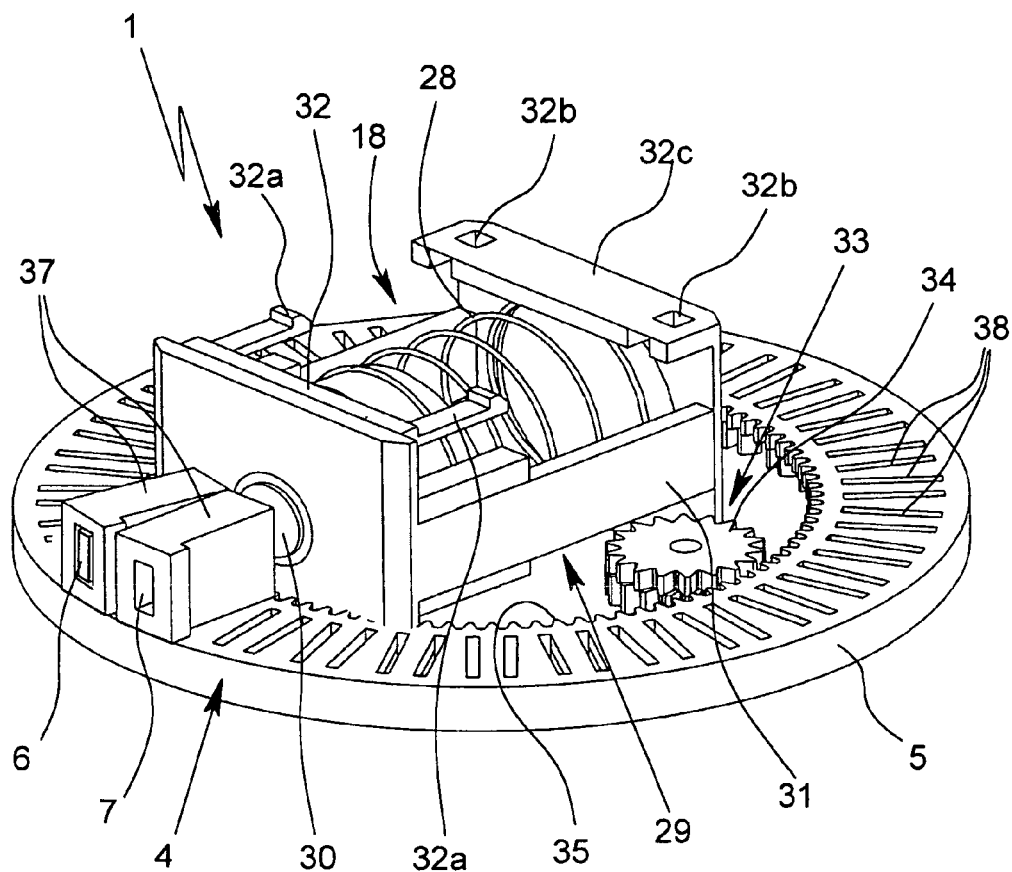
FIG. 10 a schematic perspective view of inner components of the dispensing device according to FIG. 7 with advanced air assembly after dispensing.
Figure 11:
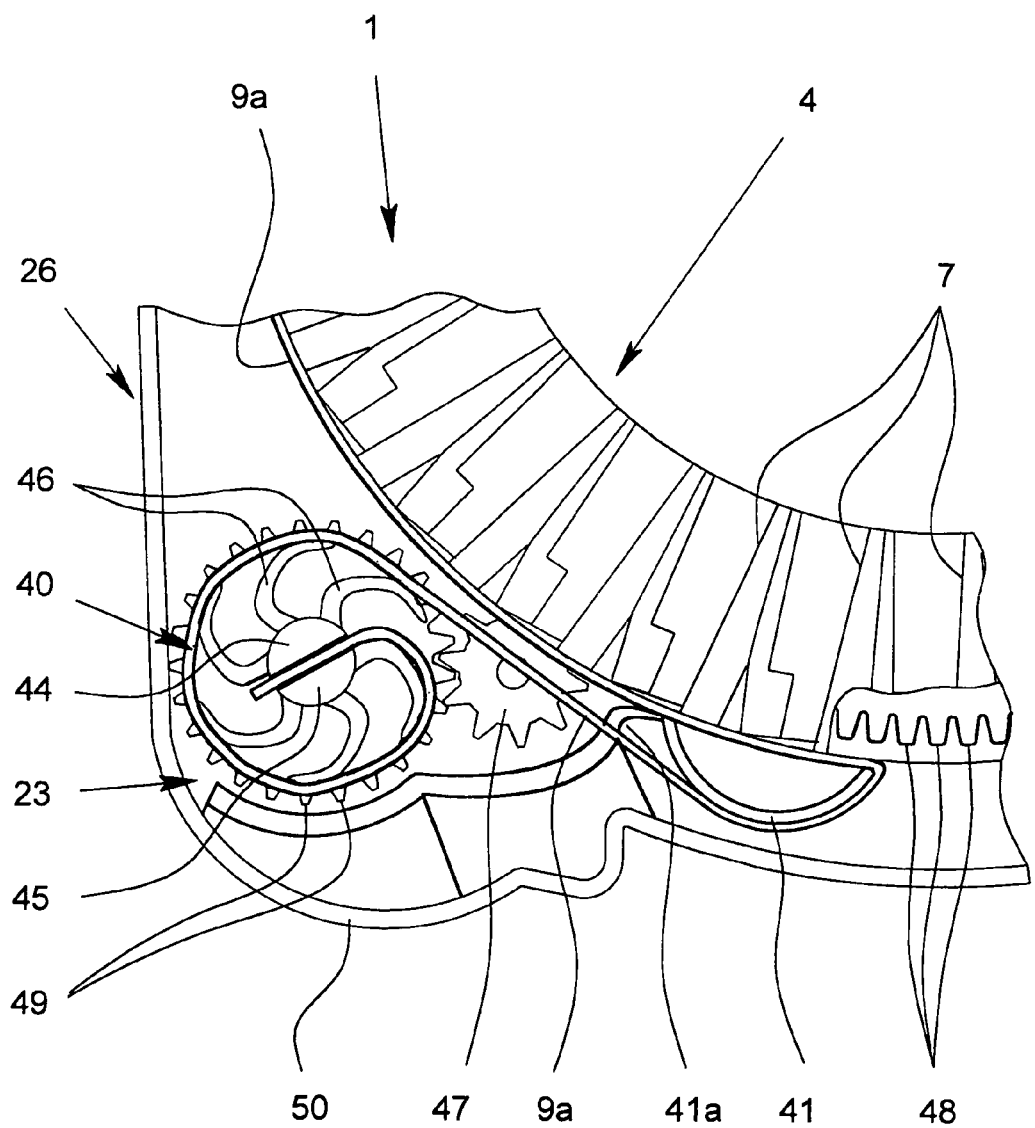
FIG. 11 a schematic partial view of the dispensing device according to FIG. 7 with an opening device.

First of all, the basic principle of the dispensing device 1 will be explained with reference to FIGS. 8 to 10. FIGS. 8 to 10 show only very rudimentary schematic views (not in scale) of inner components of the dispensing device 1 for explaining the principle. In particular, the housing 26 the grip 19, most inserts 6 and the seals have been omitted. Further, the storage device 4 is shown only in a schematic manner, in particular incompletely or partially only in FIGS. 9 & 10. In particular, multiple details, such as seals 9, outlets 15 or the like, have been omitted. The preferred construction of the storage device 4 will be explained later after explaining the basic functional principle of the present dispensing device 1.

The dispensing device 1 is an active atomizer or inhaler, preferably a dry powder inhaler. The means for pressurizing gas is preferably also constructed as air pump 18. Here, the air pump 18 comprises the bellows 27 as pumping element. However, any other suitable pumping element, such as a piston, could be used.

The dispensing device 1/air pump 18 further comprises an energy or spring store, in particular the spring 28, for actuating the pumping element, i.e., the bellows 27. The air pump 18 (bellows 27 and spring 28) is preferably radially moveable, in particular in a sliding manner or like a sled. Preferably, the air pump 18 forms a slider 29 or is supported thereof. In particular, the air pump 18 and slider 29 will be referred to as an "air assembly" in the following.

Preferably, the air assembly forms or includes the mechanism 20 already mentioned with respect to the previous embodiments. For this purpose, the air assembly preferably comprises a needle holder 30 holding the piercing element/needle 17. The piercing element 17 may be pressed and/or glued or molded into the needle holder 30. Preferably, the bellows 27 is pressed or clamped onto the needle holder 30.

The needle holder 30 preferably closes or completes the slider frame 31. For example, the needle holder 30 may comprise holds for pins of the slider frame 31, which pins may be heat-riveted.

The needle holder 30 is connected to or formed by a slider frame 31, which, in turn, holds the spring 28 and/or moveably guides a tension element 32 associated to the bellows 27 and/or spring 28.

In the illustrated embodiment, the bellows 27 is arranged between the needle holder 30 and the tension element 32. The spring 28 is arranged behind the bellows 27, e.g., on the opposite side of the tension element 32.

The tension element 32 holds the bellows 27 in order to secure the filling of the bellows 27 during pulling. Namely, the grip 19 preferably retracts the tension element 32 during pulling.

The air pump 18 or air assembly is preferably located in the center of the dispensing device 1 and/or within the storage device 4 and/or ring-shaped carrier 5 and/or is preferably radially moveable.

FIG. 8 shows the situation after the grip 19 has been pulled out. The bellows 27 is extended and filled with air. The spring 28 is compressed or tensioned, i.e., the energy store has stored energy. The tension element 32 is retracted and locked in its position to hold the spring 28 in its compressed state. The air assembly/slider 29 is retracted so that the piercing element 27 is retracted from the storage device 4, in particular, so that the storage device 4 can be indexed or moved, in particular rotated.

When the grip 19 is pushed back, preferably a transportation operation and the opening or peeling operation and a connecting operation will be performed.

In the first phase of the movement of the grip 19, a transport mechanism 33 is actuated. In particular, a cogwheel 34 of the transport mechanism 33 (shown in FIG. 9) at least temporarily meshing with a preferably inner teeth 35 of the storage device 4 or carrier 5 is rotated to move or index the storage device 4 by one insert 6 or cavity 7 and/or to the next insert 6 or cavity 7. Preferably, the next insert 6 is opened or peeled simultaneously. However, it is noted that this transportation and opening/peeling operation could also be performed partly or completely during pulling.

Preferably, after termination of the transportation and opening/peeling operation, i.e., during a second phase of pushing, the connecting operation is performed. The air assembly/slider 29 is moved forward and/or radially so that the piercing element 17 connects to the next/aligned insert 6/cavity 7. In particular, the piercing element 17 pierces into the insert 6 to connect to its storage chamber 10.

Before, simultaneously and/or subsequently the transportation operation or connecting operation, the insert 6/duct 12/outlet opening 15 is opened by the opening operation, in particular, peeling the outlet seal 9a. This situation is shown in FIG. 9.

Spring 28 is still biased or compressed. This situation is also referred to as the "activated state". The dispensing device 1 is ready for dispensing the dose of formulation 2 from the opened insert 6.

To initiate delivery (discharge) of the formulation 2 and to generate the spray 3, a release button 36 (shown in FIG. 7) or any other suitable element is actuated, in particular depressed. Thus, the tension element 32 or its associated locking means is unlocked (preferably by depressing/compressing the elastic snap arm 32a), and the spring 28 is released and compresses the bellows 27. The bellows 27 compresses the air contained therein. Thus, the air is pressed through piercing element 17 into the connected insert 6. The resulting air stream is forced through the connected insert 6, entrains the powder/formulation 2 of the insert 6 and ejects as spray 3.

FIG. 10 shows the final state after discharge. The spring 28 is expanded. The bellows 27 is compressed. The tension element 32 has been moved forward to the needle holder 30/piercing element 17. The piercing element 17 is still connected to the emptied insert 6. In this state, the dispensing device 1 can be closed and transported. Therefore, this state is referred to as the "transportation state".

For the next use, the grip 19 is pulled. In a first phase of the movement, the slider 29/air assembly is retracted together with the piercing element 17 so that the piercing element 17 is retracted from the storage device 4, i.e., out of the cavity 7 of the last insert 6. In a second phase of movement, which can also happen simultaneously, but is preferably performed after stop of the slider 29, the tension element 32 is retracted within the slider 29/slider frame 31 so that the bellows 27 is extended and the spring 28 is compressed or biased until the tension element 32 is locked in its retracted position as shown in FIG. 8. During the extension of the bellows 27, air is sucked into the bellows 27, preferably through piercing element 17 and/or optionally through a suitable inlet valve (not shown).

It is noted that the release button 36 is preferably lifted only during the last phase of pushing the grip 19. Further, the lifted or activated or primed release button 36 preferably blocks pulling of the grip 19 until the release button 36 has been actuated or depressed, i.e., until the dispensing device 1 has been triggered. In particular, the release button 36 is tilted during actuation or depressing.

In the following, further details, aspects, features and advantages of the present dispensing device 1 and/or of its components will be explained.

Preferably, the storage device 4 comprises multiple receptacles 37 respectively containing only or at least one insert 6, as schematically shown in FIGS. 8 to 10. In particular, the receptacles 37 are produced as separate parts that are placed or mounted on the carrier 5. Preferably, the receptacles 37 are engaged in or held by recesses 38 on the carrier 5.

The receptacles 37 may be made of the same material as the storage device 4/carrier 5, in particular of plastic. Preferably, the receptacles 37 are rigid and form a guide for the inserts 6. Each of the receptacles 37 comprises only one or more cavities 7 for receiving the respective insert(s) 6.

Preferably, the receptacles 37 are provided with the inserts 6 already filled with the respective dose of formulation 2 and, then, mounted on the comment carrier 5.

The receptacles 37 are preferably sealed by common seals 9*a*, 9*b*. The receptacles 37 may be sealed before or after placement on the carrier 5. The receptacles 37 are preferably sealed on opposite sides and/or on longitudinal end faces. Preferably, the receptacle 37 has an essentially cuboid and/or longitudinal form.

The carrier 5 preferably supports the receptacles 37 fixedly and/or in a form-fit manner. Preferably, the receptacles 37 are snapped on to or into the carrier 5.

Preferably, the air assembly/slider 29 and the storage device 4/carrier 5/receptacles 37 interact such that a correct alignment of the piercing element 17 and the respective receptacle 37 or insert 6 is ensured before the piercing element 17 pierces or opens the respective receptacle 37, cavity 7 and/or insert 6.

Preferably, the inserts 6 are restricted in their backward movement as already mentioned so that the piercing element 17 can be retracted and uncoupled from the respective insert in a definitive manner when the air assembly/slider 29 is retracted into the position shown in FIG. 8.

In the present embodiment, a locking means is provided for locking the tension element 32 in the retracted position. Here, the locking means comprises at least one snap hook or arm 32*a*, preferably two or more snap arms 32*a* engaging into respective undercuts, recesses or snap openings 32*b* preferably formed by or in a back shield 32*c* of the slider 29 or slider frame 31 or vice versa. However, other constructional solutions are possible.

The dispensing device 1 is preferably an active powder inhaler, i.e., the powder is discharged by pressurized gas, in particular air. Nevertheless, the dispensing operation may be triggered by the inhalation or breathing in of a patient (not shown). In particular, the dispensing device 1 may comprise detection means for detecting inhalation or breathing in and/or trigger means for triggering dispensing of the respective dose.

In case of the present preferred ring arrangement, the indexing direction extends in the tangential and/or circumferential direction. The term "indexing direction" means preferably the direction in which the storage device 4 is moved, in particular rotated, stepwise from one receptacle 37, cavity 7 or insert 6 to the next one so that the respective doses of formulation 2 can be discharged one after the other.

FIG. 11 is a partial view of the dispensing device 1 with a modified opening device 23. The opening device 23 functions basically as described with reference to FIG. 6*a*.

The wheel 40 is made preferably of two halves 44, 45 or comprises a slit in order to receive and in particular fix or clamp part (preferably, the beginning or free end) of the seal 9*a* to fix it for winding up the peeled outlet seal 9*a*. However, other concepts and solutions are possible.

The wheel 40 comprises preferably spring-like arms 46 which are elastic and arranged around the periphery and form the winding surface in particular such that a variable diameter is achieved to compensate any winding diameter required as the seal 9*a* is wound up and multiple layers of the seal 9*a* are overlaid on the wheel 40.

FIG. 11 shows the dispensing device 1 with part of the storage device 4 only in a very rudimentary manner. The inserts 6 are not shown. However, the receptacles 37 with the cavities 7 located on the carrier ring 5 are visible.

FIG. 11 shows a drive coupling between the carrier 5 and the wheel 40. In the embodiment shown, an intermediate gear 47 meshes with teeth 48 on the carrier 5 and with a gear 49 of the wheel 40 so that the wheel 40 and the carrier 5 are rotatably coupled.

FIG. 11 shows that the opening device 23 is integrated into the housing 26 and/or located outside the storage device 4/carrier 5. In particular, the opening device 23 is located within a protrusion 50 of the housing 26. However, other constructional solutions are possible as well.

In the illustrated embodiment, the guide element 41 of the opening device 23 is constructed to redirect the outlet seal 9*a* at the point of peeling by an angle of more than 90 degrees, in particular about 120 degrees or more. This facilitates the peeling or reduces forces.

The guide element 41 is preferably supported or held by a flexible holding arm 41 so that the guide element 41 can move at least somewhat in radial direction. However, other constructional solutions are possible as well.

It is noted that the outlet seal 9a is preferably strip-like and preferably forms an outer periphery of the preferably annularly arranged storage members. The outlet seal 9a seals preferably multiple or all outlet openings 8a, 15 or receptacles 37 or cavities 7. The outlet seal 9a is preferably adhered mainly or only to the receptacles 37 or the carrier 5, in particularly not to the storage members/inserts 6.

In particular, the dispensing device 1 is preferably an oral and/or active inhaler, a hand-held device and/or preferably only manually operated. Most preferably, the dispensing device 1 is a dry powder inhaler.

Individual features and aspects of the different embodiments may also be combined with one another as desired or used in other constructions of atomizers, inhalers, dispensers or the like.

Some preferred ingredients and/or compositions of the preferably medicinal formulation 2 are listed below. As already mentioned, they are in particular powders or liquids in the broadest sense. Particularly preferably the formulation 2 contains the following:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

AC-1

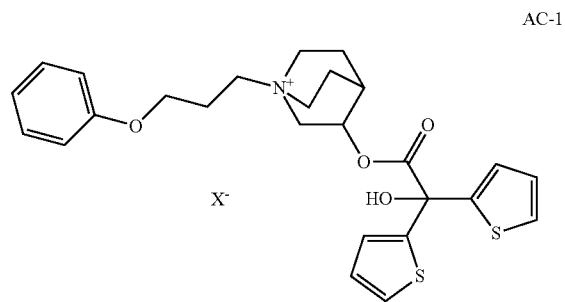

wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en AC-1-en

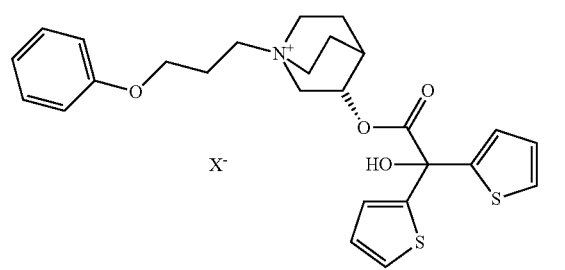

wherein X⁻ may have the above-mentioned meanings. Other preferred anticholinergics are selected from the salts of formula AC-2

AC-2

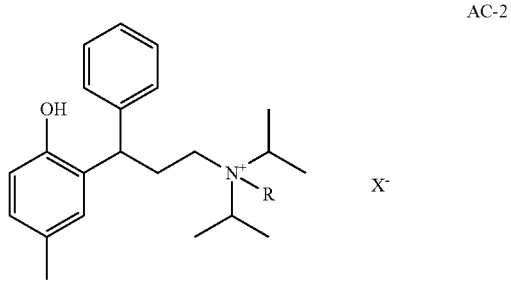

wherein R denotes either methyl or ethyl and wherein X⁻ may have the above-mentioned meanings. In an alternative embodiment the compound of formula AC-2 may also be present in the form of the free base AC-2-base.

AC-2-base

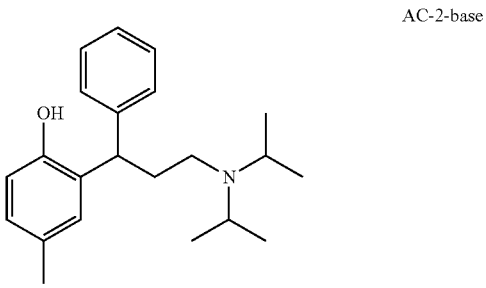 [SMILES: Cc1ccc(O)c(C(CCN(C(C)C)C(C)C)c2ccccc2)c1]

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;

cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine
optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and
1-((((R)-3-(2-(6,7-difluoro-2-quinolinyl)ethenyl)phenyl)-3-(2-(2-hydroxy-2-propyl)phenyl)thio)methylcyclopropane-acetic acid,
1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid
[2-[[2-(4-tert-butyl-2-thiazolyl)-5-benzofuranyl]oxymethyl]phenyl]acetic acid
optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and
4-[(3-chloro-4-fluorophenyl)amino]-6-{4-(morpholin-4-yl)-1-oxo-2-buten-1-yl]amino}-7-cyclopropylmethoxy-quinazoline
4-[(3-chloro-4-fluorophenyl)amino]-6-{[4-(N,N-diethylamino)-1-oxo-2-buten-1-yl]-amino}-7-cyclopropyl-methoxy-quinazoline
4-[(3-chloro-4-fluorophenyl)amino]-6-{[4-(N,N-dimethylamino)-1-oxo-2-buten-1-yl]amino}-7-cyclopropyl-methoxy-quinazoline
4-[(R)-(1-phenyl-ethyl)amino]-6-{[4-(morpholin-4-yl)-1-oxo-2-buten-1-yl]amino}-7-cyclopentyloxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-(3-ethynyl-phenyl)amino-6,7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules, as disclosed in EP 1 003 478 A1 or CA 2297174 A1.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

What is claimed is:

1. Dispensing device for dispensing a formulation as a spray, comprising:

a housing adapted to receive a storage device with multiple, separate and pre-metered doses of the formulation, an annular storage device comprising multiple rigid storage members, each storage member comprising a storage chamber containing a dose of formulation, and an atomizing device for dispensing the respective dose from the storage chamber as spray in a radial direction, wherein outlet openings of the storage members or atomizing devices are covered by a common outlet seal that is disposed on the periphery, of the annular storage device, means for pressurizing gas for generating a gas stream flowing through the storage device for dispensing a dose of the formulation, a connecting element for supplying pressurizing gas or air individually to each of the storage chambers, the connecting element being moveable in a connecting movement relative to the respective storage member for connecting to it, and an opening device for individually opening of each storage member, the opening device being adapted to work independently of the connecting movement to peel off the outlet seal from the annular storage device.

2. Dispensing device according to claim 1, wherein the outlet seal is a strip which seals multiple or all outlet openings.

3. Dispensing device according to claim 1, wherein the outlet seal is a heat-sealed foil.

4. Dispensing device according to claim 1, wherein the opening device is adapted to wind up the peeled-off outlet seal.

5. Dispensing device according to claim 1, wherein the opening device comprises a guide element for guiding the peeled-off outlet seal away from the storage members, the guide element being located adjacent to and biased against the storage members.

6. Dispensing device according to claim 1, wherein the opening device comprises a wheel for winding up the peeled-off outlet sealing.

7. Dispensing device according to claim 6, wherein the wheel is driven by or coupled with a transport movement mechanism indexing from one storage member to a next one.

8. Dispensing device according to claim 6, wherein the wheel comprises variable diameter spring-like arms for winding up the peeled-off outlet sealing.

9. Dispensing device according to claim 1, wherein the storage members are rotatable together with a carrier and wherein the opening device comprises a holding element holding a free end of the outlet seal and being mounted on a part that is counter-rotatable relative to the storage members.

10. Dispensing device according to claim 1, wherein peeling off of the outlet seal drives the storage device to index from one storage member to the next one.

11. Dispensing device according to claim 1, wherein the storage members are inserts received in separate cavities or receptacles of a rotatable carrier.

* * * * *